United States Patent [19]

Edelman et al.

[11] Patent Number: 5,527,532

[45] Date of Patent: * Jun. 18, 1996

[54] EXTRALUMINAL REGULATION OF THE GROWTH AND REPAIR OF TUBULAR STRUCTURES IN VIVO

[75] Inventors: Elazer R. Edelman, Brookline; David H. Adams, Boston; Morris J. Karnovsky, Newton Centre, all of Mass.

[73] Assignee: President and Fellows of Harvard College, Cambridge, Mass.

[*] Notice: The term of this patent shall not extend beyond the expiration date of Pat. No. 5,455,039.

[21] Appl. No.: 105,903

[22] Filed: Sep. 2, 1993

Related U.S. Application Data

[63] Continuation-in-part of Ser. No. 656,182, Feb. 27, 1991, abandoned, which is a continuation-in-part of Ser. No. 436,337, Nov. 13, 1989, abandoned.

[51] Int. Cl.$^6$ ........................................................ A61K 9/12
[52] U.S. Cl. .......................... 424/422; 424/423; 424/426; 424/430
[58] Field of Search ..................................... 424/422, 423, 424/426, 430; 514/56, 423, 12

[56] References Cited

U.S. PATENT DOCUMENTS

| | | | |
|---|---|---|---|
| 3,797,485 | 3/1974 | Urquhart | 128/213 |
| 3,993,071 | 11/1976 | Higuchi et al. | 128/260 |
| 4,391,797 | 7/1983 | Folkman et al. | 424/19 |
| 4,495,174 | 1/1985 | Allock et al. | 424/78 |
| 4,808,402 | 2/1989 | Leibovich et al. | 424/423 |
| 4,898,732 | 2/1990 | Fernandez | 424/422 |
| 5,120,322 | 6/1992 | Davis et al. | 604/265 |

OTHER PUBLICATIONS

Austin et al., "Intimal Proliferation of Smooth Muscle Cells as an Explanation for Recurrent Coronary Artery Stenosis After Percutaneous Transluminal Coronary Angioplasty," JACC 6:369–375, 1985.

Bentley et al, "An Objective Study of Alternative Methods of Heparin Administration," Thrombosis Research 18:177–187, 1980.

Bick et al., "Clinical Use of Intrapulmonary Heparin," Seminars in Thrombosis and Hemostasis 11:213–217, 1985.

Brown et al., "In Vivo and In Vitro Release of Macromolecules from Polymeric Drug Delivery Systems," J. Pharm. Sciences 72:1181–1185, 1983.

Castellot et al., "Cultured Endothelial Cells Produce a Heparinlike Inhibitor of Smooth Muscle Cell Growth," J. Cell Biology 90:372–379, 1981.

Castellot et al., "Structural Determinants of the Capacity of Heparin to Inhibit the Proliferation of Vascular Smooth Muscle Cells," J. Cell. Phys. 120:315–320, 1984.

Castellot et al., "Structural Determinants of the Capacity of Heparin to Inhibit the Proliferation of Vascular Smooth Muscle Cells." II. J. Cell Biology 102: 1979–1984, 1986.

Clowes et al., "Suppression by Heparin of Smooth Muscle Cell Proliferation in Injured Arteries," Nature 265:625–626, 1977.

(List continued on next page.)

*Primary Examiner*—Gollamudi S. Kishore
*Attorney, Agent, or Firm*—Fish & Richardson

[57] ABSTRACT

A method of regulating repair in a physiological system following injury to the lumen of a tubular structure in that system, and of testing the effectiveness of regulatory agent, is presented. The method includes administering a modulator of cell or tissue growth to an extraluminal site adjacent the injured tissue. Administration of substances such as heparin over sustained, prolonged periods controls intimal hyperplasia and smooth muscle cell proliferation, even at doses that are insufficient to have such a beneficial effect if administered systemically. Bolus administration of such compounds at higher doses typically used to achieve systemic effects may have no effect or may even produce adverse effects.

24 Claims, 2 Drawing Sheets

OTHER PUBLICATIONS

Cotran et al., "Repair by Connective Tissue–Granulation Tissue, Robbins Pathologic Basis of Disease", 4th Ed. W. B. Sanders Co., Philadelphia, pp. 73–74, 253–254, 553–557, 562–565, 1989.

Dawes et al., "Absorption of Heparin, LMW Heparin and SP54 After Subcutaneous Injection, Assessed by Competitive Binding Assay," Thrombosis Research 44:683–693, 1986.

Diaz–Flores et al., "Relation Between Arterial Intimal Thickening and the Vasa–Vasorum," Virchows Arch [Pathol Anat] 406:165–177, 1985.

Edelman et al., "Basic Fibroblast Growth Factor Enhances the Coupling of Intimal Hyperplasis and Proliferation of Vasa Varorum in Injured Rat Arteries," J. Clin. Invest. 89:465–473, 1992.

Edelman et al., "Perivascular and Intravenous bFGF Administration: Vascular and Solid Organ Deposition," Dept. of Pathology, Harvard Medical School, D2–336.

Fishman et al., "Endothelial Regeneration in the Rat Carotid Artery and the Significance of Endothelial Denudation in the Pathogensis of Myointimal Thickening," Lab. Invest. 32:339, 1975.

Gallus et al., "Prevention of Venous Thromboembolism," Seminars in Thrombosis and Hemostasis 2:232–290, 1976.

Gordon et al., "Clinical Cardiology: Restenosis After PTCA," Abstracts of the 60th Scientific Sessions, IV–213.

Guyton et al., "Smooth Muscle Cell Proliferatioin in the Occluded Rat Cartoid Artery," American J. of Pathology 94:585–602, 1979.

Grolleman et al., "Studies on a Bioerodible Drug Carrier System Based on Polyphosphazene," J. of Controlled Release 3:143–154, 1986.

Habib et al., "Preservation of Endothelium–Dependent Vascular Relaxation in Cholesterol–Fed Rabbit by Treatment with the Calcium Blocker PN200110," Circulation Research 58:305–309, 1986.

Jaques, "Drug Prophylaxis in Atherosclerosis," Artery 14:209–215, 1987.

Jaques et al., "Pharmacodynamics and Clinical Effectiveness of Heparin," Seminars in Thrombosis and Hemostasis 4:298–325, 1978.

Kakkar, "Low Dose Heparin in the Prevention of Venous Thromboembolism," Thrombos. Diathes. Haemorth. (Stuttg.) 33:87–95, 1974.

Langer et al., "Controlled Release and Magnetically Modulated Release Systems for Macromolecules," Methods in Enzymology 112:339∝423, 1985.

Langer et al., "Controlled Release and Magnetically Modulated Systems for Macromolecular Drugs," Annals New York Academy of Sciences 446:1–13, 1988.

Larsen et al., "Oral Heparin Results in the Appearance of Heparin Fragments in the Plasma of Rats," Proc. Natl. Acad. Sci. USA 83:2964–2968, 1986.

Lawter et al., "Drug Release From Poly (Glycolide–Co–DL––Lactide) Microcapsules," Proc. Intern. Symp. Control. Rel. Bioact. Matter 14:99–100, 1987.

Mahadoo et al., "Cellular Control of Heparin in Blood," Medical Hypothesis 5:835–841, 1979.

Mahadoo et al., "Endothelial Sequestration of Heparin Administered by the Intrapulmonary Route," Artery 7:438–447, 1980.

Mahadoo, "Evidence for a Cellular Pool for Exogenous Heparin," Heparin: Structure, Cellular Functions and Clinical Applications, Application Press, Inc. pp. 181–187, 1979.

Mayberg et al., "Perivascular Meningeal Projections from Cat Trigeminal Ganglia: Possible Pathway for Vascular Headaches in Man," Science 213:228∝230, 1981.

Mayberg et al., "Thrombus Prevention Without Systemic Anticoagulation: Localized Polymeric Drug Delivery of Heparin," Surgical Forum vol. XXXIX–496–499, 1988.

McBride et al., "Restenosis After Successful Coronary Angioplasty," New England Journal of Medicine 318:1734–1737, 1988.

Molino et al., "Considerazioni sull'uso dell'Eparina long––term nei cardiovasculopatici," Cardioang. 62:553–557, 1973.

Moskowitz et al., "Controlled Release of Horseradish Peroxidase from Polymers: A Method to Improve Histochemical Localization and Sensitivity," Brain Research 212:460–465, 1981.

Neenan et al., "Synthesis of a Heparinized Poly(organophosphazene)," Biomaterials 3:78–80, 1982.

Okada et al., "Localized Release of Preivascular Heparin Inhibits Intimal Proliferation after Endothelial Injury without Systemic Anticoagulation," Neurosurgery 25:892–896, 1989.

Okada et al., "Local Anticoagulation Without Systemic Effect Using a Polymer Heparin Delivery System," Stroke 19:1470–1476, 1988.

O'Reilly, "Anticoagulant, Antithrombotic, and Thrombolytic Drugs," The Pharmacologic Basis on Therapeutic, 7th ed., pp. 1338–1359, Gilman et al., eds., Macmillan Publishing Co., 1985.

Powell et al., "Inhibitors of Angiotensin–Converting Enzyme Prevent Myointimal Proliferation After Vascular Injury," Science 245:186–188, 1989.

Simons et al., "Antisense c–myb oligonucleotides inhibit intimal arterial smooth muscle cell accumulation in vivo," Nature 359:67–70, 1992.

Simpfendorfer, "Acute coronary occlusion after percutaneous transluminal coronary angioplasty," Cleveland Clinic Journal of Medicine 55:429–432, 1988.

Sparer et al., "Controlled Release from Erodible Poly (ortho ester) Drug Delivery Systems," Journal of Controlled Release 1:23–32, 1984.

Steele et al., "Balloon Angioplasty, Natural History of the Pathophysiological Response to Injury in a Pig Model," Circulation Research 57:105–112, 1985.

Stemerman et al., "Experimental Arteriosclerosis," The Journal of Experimental Medicine 136:769–789, 1972.

Whitworth et al., "Effect of Nifedipine on Recurrent Stenosis After Percutaneous Transluminal Coronary Angioplasty," JACC 8:1271–1276, 1986.

EXTRALUMINAL REGULATION OF THE GROWTH AND REPAIR OF TUBULAR STRUCTURES IN VIVO

STATEMENT OF GOVERNMENT RIGHTS

This invention was funded at least in part by the U.S. Government, and the Government, therefore, has certain rights in this invention.

CROSS-REFERENCE TO RELATED APPLICATIONS

This application is a continuation-in-part of my earlier commonly owned application, U.S. Ser. No. 7/656,182, filed Feb. 27, 1991, now abandoned, which in turn was a continuation-in-part of my earlier commonly owned application U.S. Ser. No. 07/436,337, filed Nov. 13, 1989, now abandoned.

BACKGROUND OF THE INVENTION

This invention relates to the general field of regulation of the growth and repair of tubular, or luminal, structures.

Tubular structures within the body (including bronchi of the lung, the entire gastrointestinal tract from the esophagus to the anus, the ureters and urethra of the genitourinary system, the fallopian tubes and vas deferens of the reproductive system, and the blood vessels) are all subject to luminal constriction and obstruction to flow. As a result, tissues and organs downstream of the obstruction are deprived of vital elements and tissues and organs upstream are dammed up with fluid and/or toxic products.

Surgical repair is often indicated in an attempt to relieve these obstructions. However, the repair may be unsuccessful or short-lived due to accelerated obstruction and a recurrence of the events that led to the initial crisis. Overproliferation of smooth muscle cells (SMC) as part of the natural repair process may contribute to luminal occlusion. In the arterial system, for example, restenosis rates of 25 to 35% have been noted within three months following percutaneous balloon angioplasty, and current estimates of the life expectancy of saphenous venin bypass grafts do not exceed 7 years. In the gastrointestinal system, this same phenomenon presents as recurrent bowel obstruction after lysis of adhesions or surgical anastomotic repair, and in the reproductive system as an ineffective surgical repair of the fallopian tubes or vas deferens.

There have been various attempts to limit occlusion. For example, for blood vessels, effort has been directed at various circulating (intravenous) factors such as heparin. Such factors inhibit or stimulate the clotting process and may also affect smooth muscle cell proliferation. Attempt have also been made to control environmental factors such as blood pressure, cholesterol, or smoking (nicotine). As regards lungs, attempts to limit occlusion have been directed at aerosolized factors and modulators of vascular tone (e.g., bronchodialators) and control of mucous formation. Efforts concerning the genitourinary system have focused on maintaining adequate flow, e.g. by controlling pH to enhance the solubility of stone material or by mechanical means such as ultrasound energy to break-up stones or uretal stents.

Specific animal model and tissue culture studies on limiting neointimal hyperplasia include Clowes et al. *Nature* (London) (1977) 265:625–626: Hoover et al. *Circ. Res.* (1980) 47:57814 583; Liu et al. *Circulation* (1990) 81:1089–1093; Powell et al. *Science* (1989) 245:187–189; Samembock et al. (1991) Circulation 84:232–243; Henry et al. *J. Clin. Invest.* (1981) 68:1366–1369; Jonasson et al. *Proc. Nat'l Acad. Sci.* (*USA*) (1988) 85:2303–2306.

Such studies generally have not translated into clinical success. For example, clinical use of heparin to inhibit smooth muscle cell proliferation and thereby inhibit restenosis has not met with success. Ellis et al. *Am. Heart J.* (1989) 177:777–782 report administration of heparin in 2000 iu bolus, followed by 18–24 hour intravenous administration at a dose that increased clotting time (aPP) by a factor of 1.5–2.5 relative to controls. Surprisingly, and undesirably, these heparin treated patients had a greater incidence of restenosis, as well as systemic complications not observed in the control patients and directly related to the systemic dosing with heparin. In another study, Lehmann et al. *J. Am. Co. Cardio.* (1991) 17:181A reports a similar controlled post angioplasty trial of continuous daily heparin for a month. Heparin was administered sub cutaneously (10,000 iu/day). Once again, the heparin treated patients had a higher rate of restenosis and bleeding complications compared to controls. The clinical oversight board reviewing this study terminated the study earlier than planned, because these results were so unfavorable. See also, Faxon et al. *J. Am. Coil. Cardiol.* (1991) 17:181A. Moreover, systemic administration of heparin has not reduced the rate of restenosis after coronary arterial stent placement. Serruys, et al. *N. Engl. Med.* (1991) 324:13–17; Ellis et al. *Circulation* (1992) 86:1836–1844.

SUMMARY OF THE INVENTION

We have discovered that bolus administration of heparin at doses typically used in clinical settings for systemic therapy can actually stimulate smooth muscle cell proliferation and thrombosis. On the other hand, continuous, local administration of heparin at doses too low to provide an effect if administered systemically provides substantial local antiproliferative and antithrombotic benefits in connection with luminal repair (e.g., vascular repair). These benefits are particularly obtained when the heparin is administered from the perivascular space to the vessel wall at the site of the injury. In short, the manner of administration of these compounds is critical to obtain the desired result and to avoid systemic side effects.

In general, one aspect of the invention features administering a smooth muscle cell antiproliferative agent to a patient to control smooth muscle cell growth incident to vascular injury, the agent being administered locally at a continuous sustained rate over a prolonged period of time.

In preferred embodiments, the agent is administered at a rate less than the equivalent of 20 µg/hr heparin and more preferably less than 5.0 µg/hr heparin and most preferably less than 0.5 µg/hr heparin, the agent is delivered locally to a site of vascular injury (preferably from the perivascular space at the site of the injury); the agent is administered substantially continuously over a period of at least 5 and most preferably at least 10 days. For example, the agent is administered without a significant (e.g. no more than 6 hours and preferably no more than 3 hours) gap in administration. Most preferably, the agent is administered from a controlled release device, such as a controlled release polymer formulation or an infusion pump.

The invention enables administration of anti-proliferative agents at dosages insufficient to create the desired beneficial effects if infused systemically. In some cases the invention involves dosages three or four orders of magnitude lower than levels achieved with systemic therapy. Dosages as low as 6 ng/hr from a perivascular controlled release device produced marked suppression of intimal hyperplasia.

A second aspect of the invention features a method of regulating repair following injury to luminal tissue that includes administering a modulator of cell or tissue growth at an extraluminal site adjacent the injured tissue. "Regulating repair" is meant to include controlling luminal occlusion (e.g., the reduction or the prevention of formation of such occlusion). By luminal tissue is meant the tissue, primarily endothelium, in the lumen of a tubular structure. A modulator is an agent that effects a change in the rate of cell or tissue growth. An extraluminal site is one located outside and adjacent to the injured tubular structure, one example being the adventitia, the layer of loose connective tissue forming the outermost coating of an organ.

Preferred embodiments of the invention include the following features. The invention is particularly appropriate for controlling repair of the vascular system, preferably repair of an artery, and the preferred modulating agent is either anticoagulant or non-anticoagulant heparin. The modulator preferably is delivered to the adventitia adjacent the artery from a polymeric formulation (e.g., an ethylene-vinyl acetate copolymer matrix), at a rate of from 1 µg to 100 mg/day, for a period of at least 24 hours. Preferably, dosage is below the limits described above regarding the first aspect of the invention. Other sites of injury for which the method is particularly appropriate include the fallopian tubes or the vas deferens of the reproductive system, the ureter or the prostate gland of the genitourinary system, the bowel of the gastrointestinal system, or the trachea or the bronchial tree of the pulmonary system. Other vehicles for administration include aqueous gels, foams, or sprays (e.g. aerosolized).

In a third aspect, the invention generally features a method of testing the effectiveness of a modulator in regulating repair following injury to luminal tissue that includes administering the modulator to an extraluminal site adjacent the tissue and determining the extent of regulation of repair following such administration.

Local administration of a modulating agent to an extraluminal site adjacent an injured luminal structure or organ allows for orderly repair of the injured endothelium while reducing detrimental side effects of other forms of administration.

Other features and advantages of the invention will be apparent from the following description of the preferred embodiment thereof, and from the claims.

DESCRIPTION OF THE PREFERRED EMBODIMENT

Figure 1:
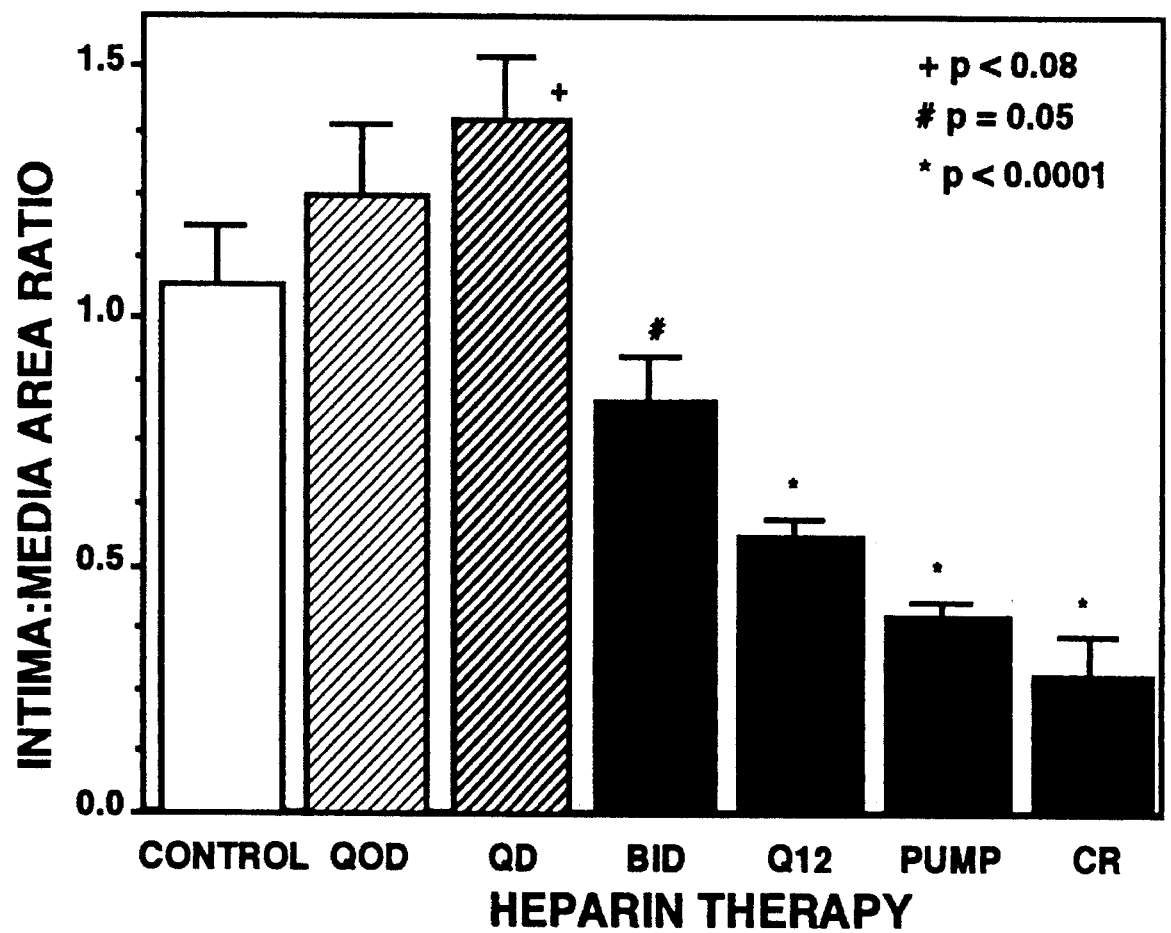
FIG. 1 is a bar graph showing the effect of different modes of heparin administration on intimal hyperplasia after injury to the arterial intima.

The method of the invention permits local administration of a modulator of cell or tissue growth to the outside of a tubular (or luminal) physiological structure for the purpose of regulating the repair of that structure following injury, for example, by surgical procedures. Examples of systems containing such structures and typical surgical procedures where regulating the repair process would be valuable are the vascular system (e.g., vascular anastomoses that accompany procedures such as organ transplant, coronary by-pass surgery, systemic arterio-arterio and arterio-venous bypass surgery, and arterio-venous shunts that accompany vascular access for dialysis); the reproductive system (reversal of tubal ligation or vasectomy); genitourinary system (prostate surgery); gastrointestinal system (anastomotic repair of a bowel obstruction); and the pulmonary system (repair or reconstruction of traumatic or surgical injury to tracheal or bronchial structures).

A wide range of growth modulating agents are appropriate for use in carrying out the method of the invention including those indicated as affecting angiogenesis, smooth muscle cell proliferation or vascularization. Some examples (as described in more detail below) include: heparin; the angiotensin converting enzyme inhibitors (e.g., captopril); angiotensin; angiogenic growth factors; heparin binding growth factors (See U.S. Pat. No. 4,882,275), particularly fibroblast growth factor; platelet derived growth factor (PDGF); transforming growth factor-β(TGF-β); immunosuppressants (e.g., cyclosporine); calcium channel inhibitors (e.g., nifedipine); as well as cytokines and interleukins which control cell-cell interaction during vascular or other luminal tissue repair in response to injury.

The modulator may be delivered to the appropriate site outside the tubular structure of interest in a delivery system, e.g., a formulation composed of the modulator in solid form and a polymer, such as an ethylene-vinyl acetate copolymer (described in detail below). The delivery system can be made from any generally inert biocompatible material. The material can be formed in a matrix as described below, or it can be in capsule form or other known configurations for sustained controlled local release such as gels, foams, wraps, or beads. Desired kinetics for the release of a particular drug can be achieved by known techniques by controlling fabrication techniques or the nature of the polymeric material of the delivery system.

A polymeric system for the delivery of the modulating agent is particularly useful when the substance to be delivered is unstable in solution, rapidly degraded, prone to precipitation, or of limited solubility. Alternate delivery systems which may be especially appropriate for modulating agents include bioerodible systems such as polyorthoester systems described in Sparer et al., *J. Controlled Release* 1: 23–32 (1984); poly (glycoside-CO-DL-lactide) microcapsules disclosed in Lawter et al., *Proc. Int'l. Symp. Control. Rel. Bioact. Mater.* 14:99–100 (1987); and poly (organophosphazene) bound drugs as disclosed by Neenan and Allcock, *Biomaterials* 3: 78–80 (1982), and Grolleman et al., *J. of Controlled Release* 3: 143–154 (1986).

A particularly preferred polymer release matrix is the ethylene-vinyl acetate copolymer (EVAc) matrix described in Folkman and Langer U.S. Pat. No. 4,391,797, hereby incorporated by reference. One specific configuration of the polymer matrix features a torroidal shape, so that the matrix can surround the outside of the artery or other luminal tissue being treated. A wicking device may be included in the matrix to enhance delivery to the hole in the center of the matrix. The outside of the matrix is coated (e.g., with unloaded polymer to avoid release from the outside matrix surfaces. Such a device is described in WO91/07154, hereby incorporated by reference.

A particularly preferred cell and tissue growth modulating agent is heparin, an α,β-glucosidically linked, highly sulfated copolymer of uronic acid and glucosamine. Preparations are polydisperse with a molecular weight range of from 5,000–40,000 daltons. The precise composition of commercial heparin and the precise degree of antiproliferative activity vary depending on the source and method of purification. By the term "heparin," we mean to include all forms of heparin and all fragments of heparin having an antiproliferative effect, e.g., both anticoagulant heparin and non-anticoagulant heparin (e.g., heparin that is identified by its failure to bind to an anti-thrombin III affinity column) have antiproliferative activity. Other well known methods of preparing non-anticoagulant heparin include modification of native heparin by periodate oxidation or by enzymatic degradation, and de novo synthesis.

To establish loading of a matrix, drug release in vivo from the matrix (e.g. an EVAc matrix) is assumed to mirror release in vitro (Brown et al., *J. Pharm. Sci.* 72:1181–1185 (1983)). The maximum number of units of modulator to be applied directly to the extraluminal tissue (e.g., an arterial wall) can be estimated by using in vitro release data. Animal models such as those described below provide a dose response curve. To scale up from animal to human delivery, e.g., in human arteries, one considers only the difference in vessel wall size (tissue thickness). For example, scaling up from rat to human vessel diameter involves a factor of only approximately four to ten-fold). Because achieving systemic effects is not desired, body weight does not enter into the calculation.

Specifically, the preferred antiproliferative agent is heparin. Heparin is loaded into a prolonged release device, such as a polymer formulation, so as to produce a release rate as described above.

At the time of surgical intervention, the polymer formulation embedded with the modulator is placed at an extraluminal site (e.g., in the adventitia) adjacent the injured lumen (e.g., artery) and the adjacent muscles and facia are sutured closed to insure immobilization of the matrix. Heparin is released from the matrix to the blood vessel. For example, with some such polymer systems, such as EVA, fluid is absorbed by the matrix and solubilizes the modulator, which then diffuses in solution through the channels of the matrix and out into the adventitia. Positioning of the matrix in the adventitia assures that heparin delivery takes place at the exterior surface of the blood vessel wall, at the site of injury.

A particular feature of the invention is local controlled release over a prolonged period of time to provide for local repair at dosages which, if administered systemically, would not have the desired effect. As noted above, the preferred smooth muscle proliferation control substance is heparin, preferably anti-coagulant heparin. The preferred method for delivery is a sustained release polymer formulation as described above. The release rates used according to this aspect of the invention are generally lower than any previous data regarding systemic release would predict to be effective. For example, release rates less than 20.0 µg/hr heparin and more preferably less than 5 µg/hr heparin and even below 0.5 µg/hr heparin are effective. Rates of 6 ng/hr are effective. It is preferred that the release rate be at least 0.1 ng/hr.

Release is prolonged beyond the time previously thought to have an effect on repair. Smooth muscle proliferation continues for several weeks after injury, more severe injuries resulting in more prolonged smooth muscle cell proliferation. For more superficial vessel injuries (e.g., after balloon angioplasty), release should continue for at least one week. For severe injuries (e.g., after coronary arterial stent), release should continue for several weeks and even up to a month.

Example 7 below demonstrates that continuous heparin administration is substantially superior to periodic bolus administration in the inhibition of smooth muscle cell proliferation and in the inhibition of intimal hyperplasia, especially when the dosage was administered locally and was below dosages that would have the desired effect if administered systemically. The dosages administered continuously in the experiments of Example 7 were 0.3 mg/kg/hr (PUMP) and 2.16±0.14 µg/kg/hr (CR). Similar experiments show that even lower doses are also effective for inhibiting intimal hyperplasia and cell proliferation. Continuous release can provide beneficial effects at dosages too low to cause increased clotting times or other undesired side effects.

Without wishing to bind ourselves to a specific theory, we note that intermittent administration of heparin results in significant oscillations in the systemic thrombotic state (as determined by aPTT), spanning a 3–4 fold range with marked anti-coagulation in one part of the day and complete recovery in the other. The deleterious effect of intermittent heparin therapy may reflect the results of cyclical variations in clotting. Alternatively, the deleterious effect may simply reflect periods of time without the beneficial effects of heparin's presence. Finally, there are reports that venous thrombosis and arterial disease (e.g., unstable angina) become unstable or are reactivated when heparin is removed. This so-called heparin rebound may also play a part in the deleterious effect of intermittent heparin administration. Whatever the mechanism underlying this phenomenon, heparin administration according to the invention provides clear benefits that are not attainable or predictable from intermittent bolus administration.

Another specific illustrative, non-limiting example of this aspect of the invention is provided by Example 8, below.

The following examples of specific procedures, modulators and delivery systems used in animal models are provided to illustrate and not to limit the invention.

EXAMPLE 1

Heparin, particularly non-anticoagulant heparin, can be administered to an artery from an EVAc slow release matrix according to the following example.

An EVAc matrix loaded with 0.1–1000 mg (most preferably 0.5–500 mg) non-anticoagulant heparin is prepared as described below. As part of the surgical procedure, (e.g. coronary by-pass or coronary valve replacement) the matrix is sutured in the adventitia adjacent the artery. The adjacent muscles and facia are sutured closed to immobilize the matrix adjacent the arterial repair. The heparin is released at a rate of 1 µg –100 mg/day, for more than one (preferably more than three, and most preferably more than seven) days.

EXAMPLE 2

Anti-coagulant (AC) heparin (Choay Heparin 1453, m.w. 12,000–18,000 dalton, U.S.P. 160 U/mg, in vitro antiproliferative activity 80% (as described by Castellot et al. (1987) *Seminars in Thrombosis and Hemostasis* 13: 489–503) or non-anti-coagulant (NAC) heparin (Choay heparin 1772, m.w. 5000–8000 dalton, U.S.P. 10 U/mg, in vitro antiproliferative activity 80%), Choay Institute, Paris, France, were embedded in polymer matrices using a solvent casting technique as described in Langer et al., *Methods in Enzymol.* 112:399–423 (1985). First, ethylene-vinyl acetate copolymer (ELVAX-40P, 40% vinyl acetate, E. I. DuPont, Wilm., Del. or U.S.I. of Cincinnati, Ohio) was dissolved in methylene chloride to a concentration of 10% (w/v). Dry powdered heparin was then sieved to particle sizes less than 180 microns and added to the EVAc solution. If the heparin aggregated, the drug was dissolved in normal saline, lyophilized to a powder, pulverized with mortar and pestle in a humidity controlled box and then sieved and added to the dissolved EVAc. The drug-polymer suspension was vortexed, let stand for 15 seconds to allow air bubbles to settle out and then poured into glass molds that had been precooled on dry ice. At these temperatures, the heparin was immediately frozen in place so as to be uniformly distributed through the matrix and not settle on the bottom. The resultant matrix was a homogeneous dispersion of heparin within EVAc. Once hardened, the matrices were removed from their glass molds, placed in a −20° C. freezer for two days and then under vacuum (600 mtorr) for another two days.

For use, smaller pellets were cut from the larger slabs to specific sizes and weights, and a coating was applied by placing a 20 gauge intravenous needle one cm into the center of the face of the matrix pellet and then immersing the pellet in a solution of 10% EVAc dissolved in methylene chloride for 5 seconds. As the pellets were withdrawn from the solution, they were spun slowly for a minute to allow for uniform coating. This entire process was repeated twice more. The matrices were left on the needles and placed in a chemical fume hood to allow for further solvent evaporation. After 12 hours, the extraneous polymer material that had migrated up the needle was removed by spinning a tweezers around the base of the needle as it was withdrawn from the matrix pellets. This insured that the extra polymer material did not collapse over the hole and that the hole remained open. Matrices were stored in a desiccator where solvent evaporation continued to completion.

Male Sprague-Dawley rats (300–500 gm, Charles River Breeding Laboratories, Wilmington, Mass.) were anesthetized with sodium nembutal 0.5 mg/gm body weight, and supplemental anesthesia was maintained with ether inhalation. A midline incision was made from the mandible to the mid-sternum. The carotid artery was exposed along the length of the bifurcation with blunt dissection, and the external carotid artery was isolated and ligated in its cephalad portion. A 2 French Fogarty balloon catheter (American Edwards Laboratories, Santa Ana, Calif.) was introduced into the arteriotomy of the external carotid artery and passed in its inflated state over the endothelium of the common carotid artery three times. The catheter was then deflated and removed from the external carotid artery, which was then ligated. As a control, the contralateral artery underwent identical manipulation, save for the introduction of the balloon catheter. In different groups of animals, EVAc matrices containing no drug, AC heparin or NAC heparin were placed adjacent to the injured artery. The adjacent muscles and fascia were sutured closed with 4–0 nylon suture to insure immobilization of the pellet. The midline incision was closed with the same suture and animals observed in separate cages during recovery. As a control, to demonstrate that the effect at issue is specific for adventitial or extraluminal delivery, EVAc matrices were placed in a subcutaneous pocket over the animal's dorsal neck region. In other animals, an osmotic infusion pump (ALZA Corporation, Palo Alto, Calif.) provided continuous iv administration of these same agents. The pump was placed in a pocket made in the neck of the rat, and a silastic catheter extended from the pump to the right internal jugular vein. AC and NAC heparins were mixed in lactated Ringer's solution and delivered at 0.3 mg per kilogram of body weight per hour. Control animals received lactated Ringer's infusion. The overall doses of the drugs administered are displayed in Table I.

TABLE I

| | HEPARIN DOSAGE mg (over 14 days) | | | | | |
|---|---|---|---|---|---|---|
| | | | MATRICES | | | |
| | INTRAVENOUS | | CAROTID | | DORSAL | |
| NAC | (5) | 25.9–43.3* | (10) | 19.5 ± 1.9 | (5) | 18.5 ± 2.9 |
| AC | (5) | 25.9–43.3* | (8) | 8.1 ± 1.9 | (4) | 7.1 ± 0.2 |

*set to 0.3 mg/kg/hr and dictated by the size of the animal numbers in parentheses represent the number of animals in each group As an indication of anti-coagulation activity, activated partial thromboplastin times (aPTT) were determined within the first 24–36 hours after the procedure and at day 14. To observe the percent of luminal occlusion, animals were euthanized while undergoing intravascular fixation perfusion using methods described in A. W. Clowes et al., *Lab. Invest.* 49:327 et seq. (1983). Photomicrographs of all arterial sections were obtained, and the percent of luminal occlusion was calculated for each arterial segment using computerized digital planimetry. Specifically, the natural lumen boundary is apparent by photomicroscopy. The boundary is extended inwardly by inclusions. Digital planimetry is used to provide a measure of the cross-sectional area of the natural lumen boundary, divided into the area of the inclusion, yielding percent occlusion.

Anti-coagulation activity as given by the aPTT (Table II) and extent of luminal occlusion (Table III), for each animal group, are detailed below.

TABLE II

| | aPTT (sec) | | | | | |
|---|---|---|---|---|---|---|
| | | | MATRICES | | | |
| | INTRAVENOUS | | CAROTID | | DORSAL | |
| CONTROL | (6) | 16.2 ± 0.1 | (8) | 16.5 ± 0.4 | | |
| NAC | (5) | 18.4 ± 0.6 | (10) | 15.0 ± 0.4 | (5) | 17.5 + 0.5 |
| AC | (5) | 40.0 ± 11.8* | (8) | 15.3 ± 0.1 | (4) | 17.0 ± 1.0 | numbers in parentheses represent the number of animals in each group
statistical significance compared with corresponding controls: *p<0.0005

TABLE III

| | | LUMINAL OCCLUSION (%) | | | | |
|---|---|---|---|---|---|---|
| | | MATRICES | | | | |
| | | INTRAVENOUS | | CAROTID | | DORSAL |
| CONTROL | (6) | 52.2 ± 4.2 | (8) | 55.9 ± 4.3 | | |
| NAC | (5) | 46.4 ± 3.9 | (10) | 17.7 ± 3.78@ | (5) | 45.0 + 2.0 |
| AC | (5) | 16.8 ± 4.3** | (8) | 9.4 ± 2.6* | (4) | 28.0 ± 2.6 | numbers in parentheses represent the number of animals in each group
statistical significance compared with corresponding controls:
*p<0.0005, **p<0.0003, @p<0.0001

Referring to Table II, only the intravenous administration of AC heparin produced systemic anti-coagulation. Neither the local matrix delivery of either heparin, in subcutaneous or adventitial positions, nor the intravenous infusion of NAC heparin had any discernable effect on clotting function. None of the animals in any groups suffered from excessive bleeding. Referring to Table III, intravenous AC heparin infusion reduced luminal occlusion 68%, from a control value of 52.2 to 16.8%. NAC heparin delivered in the same fashion achieved only an 11% reduction (no statistical difference in comparison to control). Subcutaneous matrix delivery of NAC heparin also showed no significant difference in luminal occlusion, but similar delivery of AC heparin reduced occlusion by 52%. The largest effect on luminal occlusion was observed with adventitial delivery. Occlusion was reduced from 55.9% to 9.4% (83% reduction) in animals with AC heparin matrices, and to 17.7% (68% reduction) in animals with NAC heparin matrices.

EXAMPLE 3

To generate a dose response curve for NAC heparin, twelve rats were implanted with NAC heparin-bearing matrices of different net weights so as to deliver different dosages of heparin over the 14 day period. As the dose of the NAC heparin was increased, the effect on SMC proliferation rose, such that at the highest dose tested, NAC heparin inhibited SMC proliferation to an equal extent as AC heparin, at five times the equivalent dose. A dose response experiment was not performed for AC heparin as the amount of heparin delivered in the uniform dose study was already low and had achieved over 80% inhibition of SMC proliferation.

At a rate of about 0.8 mg/day for in vitro release, the maximum amount of heparin human arteries would be exposed to would be no higher than 20–50 units/hour, and systemic levels would be undetectable. This is in marked contrast to the 1000–1500 units/hour of i.v. infusion currently used in clinical practice for systemic anticoagulation.

In vitro release kinetics were defined for five flat slab (15, 30 or 50% heparin:EVAc w/w), and for five slabs coated with plain EVAc (at 15 or 30% concentration) with a hole drilled into one face. Uncoated matrices exhibited first order release kinetics with the bulk of the drug eliminated in the first 24 to 48 hours. At higher matrix concentrations, heparin was released more rapidly and to a greater extent. When a coating was applied and release constrained to emanate from a hole drilled into the coated polymer face, the initial burst of release was eliminated but overall amount delivered sustained.

EXAMPLE 4

Angiotensin-converting enzyme inhibitors have a profound effect in lowering blood pressure, primarily through vasodilation. Independent of this hemodynamic effect, the most potent compounds in this class have been shown to inhibit luminal occlusion from smooth muscle cell proliferation during repair following balloon injury when administered orally (Powell et al., Science 245: 186–189, 1989).

The local, extraluminal action of the least potent of this class of agents, captopril, was studied in the balloon injury/polymer matrix/adventitial delivery model described above. Powdered captopril (Capoten®, Squibb Pharmaceuticals) was embedded within EVAc matrices at 50% loading and delivered at a dosage of 10.79±0.1 mg, over the course of 14 days, to the adventitia of the carotid artery. The percent of luminal occlusion was 37.7±3.0.

EXAMPLE 5

Angiotensin II (AII) has been demonstrated to have both inhibitory and stimulatory effects on SMCs in tissue culture and has also been demonstrated to induce blood vessel growth in avascular structures such as the rabbit cornea, independent of its hemodynamic effects. Matrices of ethylene-vinyl acetate copolymer were embedded with AII and sustained first order release demonstrated for more than one month. As the drug is potent in ng quantities, the EVAc matrix drug embedding technique was modified to include bovine serum albumin (BSA) as a carrier compound. When dry powdered AII was mixed with dry powdered BSA in a 1 to 500 ratio and then embedded within a EVAc matrix, the rate of BSA release dictated the rate of AII release. When this system was then placed in the balloon injury model described above, the vascular occlusion was noted and the number of blood vessels surrounding the implant counted and compared to control.

DOSE: 17 µg over the course of 14 days
LUMINAL OCCLUSION: 22.5–64%
INHIBITION COMPARED TO CONTROL: 0–62.6%
NUMBER OF VESSELS SURROUNDING AII IMPLANT: 27
NUMBER OF VESSELS SURROUNDING CONTROL IMPLANT: 6

Angiotensin II was able to induce a marked vascular response regardless of its ability to control SMC proliferation.

EXAMPLE 6

Heparin binding growth factors such as fibroblast growth factor (FGF) in culture are mitogens for a number of cell types and a potent angiogenesis factor in vivo that has no apparent effect on blood pressure. As growth factor activity may be lost if the factor is embedded in standard controlled release devices, an alternative method was used, taking of advantage the inherent ability of such growth factors to adhere to heparin.

FGF (Takeda Industries, Japan) was bound to heparin sepharose beads to stabilize the factor and to provide a solid carrier for minute quantities of the liquid growth factor. Aliquots of FGF were mixed with 2 ml of $I^{125}$FGF (1.2 mg/ml) and then incubated for 1 hour with the heparin sepharose beads. Subsequent release of FGF from the beads was followed in 0.15M NaCl buffer. Microspheres containing FGF were constructed by dropping a mixture of sodium alginate (1%) with heparin sepharose bead-bound FGF through a glass Pasteur pipette into a hardening solution of calcium chloride (1.5 weight %). Release kinetics were determined for microcapsules containing 6 ml of FGF and 2 ml of $I^{125}$FGF bound to 125 mg of the heparin sepharose beads in 500 ml of 0.15M NaCl. Heparin sepharose bead-laden FGF was incorporated within alginate microcapsules with 74% efficiency, and release of the FGF over time was retarded and prolonged in comparison to release from the unencapsulated beads. Bioactivity was retained by 87.6±12% of the factor preparation. Microspheres prepared as above were placed adjacent to noninjured and balloon endothelialized carotid arteries. In both blood vessels a significant increase in local vascularity was noted.

In addition to the examples described above, the method can be used in a laboratory setting to test the luminal repair-enhancing effect of a variety of potentially potent cell or tissue growth modulators previously discarded as ineffective because they do not act systemically, do not act in a similar fashion over a range of dosages, are degraded before they achieve their effects if applied systemically, or have side effects when delivered systemically.

EXAMPLE 7

A. Summary

The following example demonstrates the effectiveness of different heparin administration regimes for inhibiting intimal hyperplasia and smooth muscle cell proliferation following arterial injury. Heparin was administered according to the following six regimes: a) QOD (once every other day); b) QD (every day); c) BID (twice a day spaced approximately 7 and 17 hours apart); d) Q12 (every 12 hours); and continuously through e) (PUMP) an implanted osmotic minipump or f) (CR) a polymeric controlled release matrices.

Figure 2:
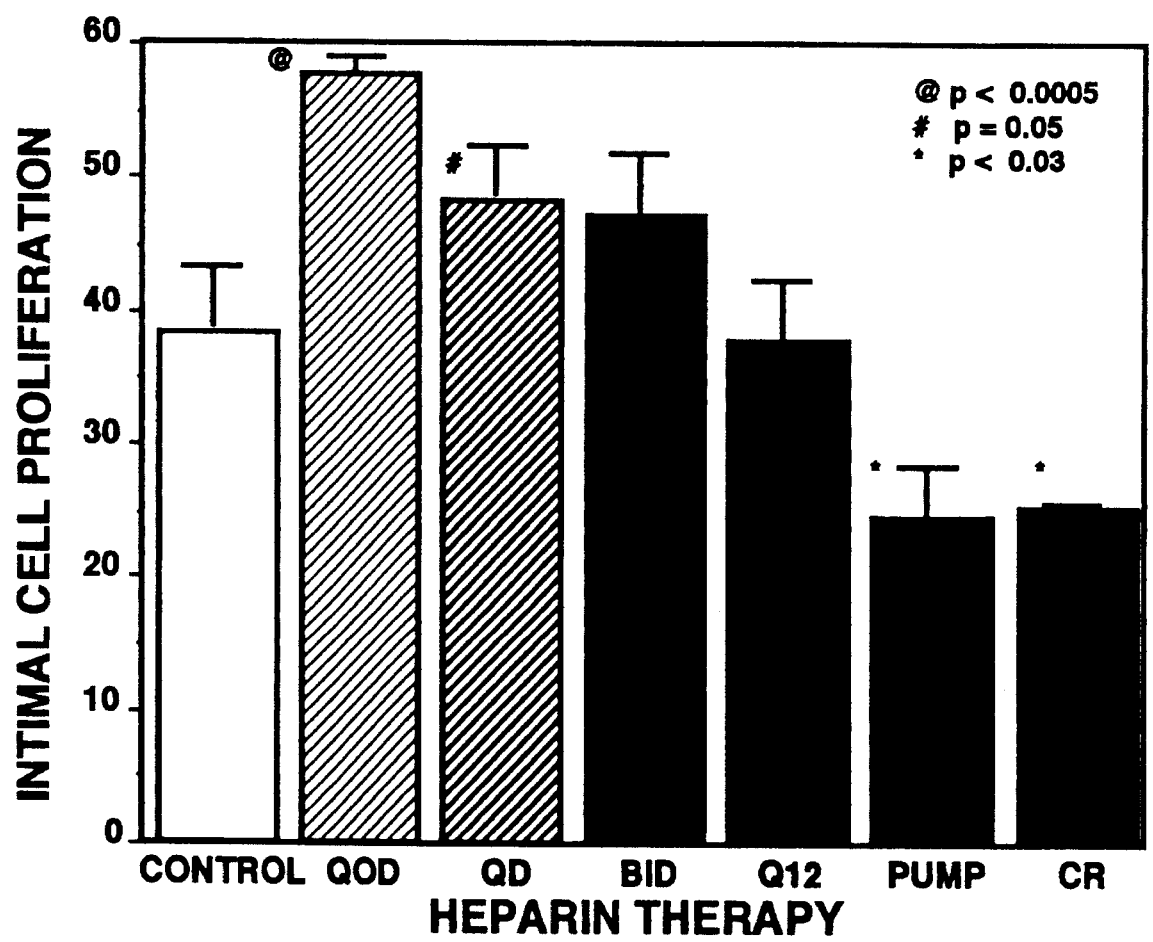
FIG. 2 is a bar graph showing the effect of different modes of heparin administration on intimal cell proliferation after injury to the arterial intima.

Inhibition of intimal hyperplasia was determined by inspection of the arteries post mortem (FIG. 1). Smooth muscle cell hyperplasia was determined by following intracellular appearance of the thymidine analog 5-bromo-2'-deoxyuridine (BrdU) after injection of BrdU (FIG. 2).

Bolus (subcutaneous injection) of heparin every other day, every day and even twice daily at uneven spacing exacerbated, rather than alleviated, intimal hyperplasia and smooth muscle cell hyperplasia following arterial injury. It was not until the heparin was administered at 12 hour intervals that intimal hyperplasia and smooth muscle cell proliferation were lessened. Continuous release provided substantial benefit over controls and even over Q12 administration.

The details of this experiment are given below.

B. Methods

1. Vascular Injury and Heparin Therapy

A balloon catheter was used to denude the endothelium from the inside of the carotid arteries of rats as described previously. Starting immediately post-injury animals received subcutaneous injections of heparin (55.5 IU equivalent to ~1.0 mg/kg) once every other day (n=7, QOD), once a day (n=7, QD), twice a day spaced approximately 7 and 17 hours apart (n=7, BID), or every 12 hours (n=7, Q12). Separate groups of animals received heparin continuously from implanted osmotic mini-pumps with indwelling intravenous catheters (n=7, PUMPS) or from polymeric controlled release matrices residing in the perivascular space (n=7, CR). Pump infusion was set at 0.3 mg/kg/hour corresponding to the effective dose previously documented to have a substantial inhibitory effect on intimal hyperplasia. Upon tissue harvest the pumps were retrieved, and the veracity of release and verification of rates determined by examining the heparin content within the pump reservoir residual volume. Polymer matrices were constructed from ethylene-vinyl acetate copolymer (EVAc) as generally described elsewhere. Heparin was mixed with a solution of EVAc dissolved in dichloromethane (10% w/v) to achieve a final ratio of 33% w/w. The drug-polymer suspension was poured into precooled glass molds, removed after hardening, and placed at −20° C. and then under vacuum (600 mtorr) for two days each. The resultant matrix was a homogenous dispersion of drug within a porous network of EVAc. Smaller pellets were cut from the larger slabs and coated with six layers of EVAc. Drug release was restrained to emanate from a hole in the coating and near zero order kinetics obtained in this fashion. Matrices were pre-released for 4 hours in sterile water to allow for any burst of release to occur and for linear release to commence. As with the pumps, matrices were retrieved at the time of tissue harvest, the heparin extracted and total amount released determined using the Azure-A colorometric assay, and compared to in vitro release rates from identical matrices. In this manner we determined that the matrices were releasing heparin at 2.16±0.14 mcg/kg/hr during the linear phase of drug release; almost 140 fold less heparin than what was administered intravenously.

The amount of heparin injected was calculated from the amount of heparin used in clinical trials that had shown exacerbation. In those trials 10,000–125,000 IU of drug were injected or infused daily. Accordingly, we scaled down for animal weight and injected animals with 55.5 IU/injection (~1.0 mg/kg). In other animals the amount of heparin injected subcutaneously was increased to the amount of drug that would be delivered over that period of time if infused from the pumps; 7.2 mg/kg/day. Finally, in an effort to determine whether pre-existing drug levels might be beneficial, daily heparin injections were initiated a full week before the arterial injury was imposed. Four sets of control animals were used, including animals with no therapy after balloon injury, animals receiving injections of saline, animals in whom implanted pumps delivered Ringer's lactate at the identical rate to the volume delivery of heparin, and animals implanted with an EVAc matrix without heparin.

2. Tissue Processing and Analysis

On the 14th post-operative day animals were euthanized and perfused clear retrograde via the left ventricle with Ringer's lactate solution followed by immersion fixation with Carnoy's fixative (60% methanol., 30% chloroform, 10% glacial acetic acid). The location of the implanted devices was noted and the devices recovered with the intact arteries. Both common carotid arteries were harvested and cut into three equal segments. The segments were paraffin embedded and microtome sectioned. Eight to 12 sections along the length of each segment were obtained, and stained with Hematoxylin/Eosin or verHoeff's elastin stain. The intimal, medial and adventitial areas, the intima:media area ratio and the percent of luminal occlusion were calculated for each arterial segment using computerized digital planimetry with a dedicated video microscope and individualized software. The averages of all sections and segments used for comparison. Edge detection software was further used to detect cell number within 8–32 sections per media or intima and when combined with area data used to determine cell density. All analyses were confirmed by visual inspection and the accuracy of the system verified with a series of matched manual cell density determinations.

Cell proliferation was followed by injecting the thymidine analog 5-bromo-2'-deoxyuridine (BrdU, New England Nuclear, Dupont Corp., Del.) intraperitoneally, at 50 mg/kg, 3 and 7 days post-surgery and one hour prior to sacrifice. Intracellular BrdU was identified immunocytochemically as generally described by Edelman et al. (1992) *J. Clin. Invest.* 89:465–471, using a mouse IgG anti-BrdU antibody diluted 1:50 (Coulter Immunology, Hialeah, FL), and peroxidase labeling with avidin-peroxidase complex (Vector Laboratories, Burlingame, Calif.) and 3,3'-diaminobenzidine (Sigma Chemical Co., St. Louis). Sections were counterstained with methyl green or hematoxylin.

Data are presented in Table IV, below. Data are presented as the mean±standard error. Statistical comparisons were performed with non-paired t-test for groups of unequal sample sizes, and data was rejected as not significantly different if p values of greater than 0.05 were observed.

TABLE IV

EFFECTS OF DAILY INJECTIONS OF HEPARIN ON INTIMAL HYPERPLASIA AND SMOOTH MUSCLE CELL PROLIFERATION FOLLOWING ARTERIAL INJURY

| mg/kg/day | n | INTIMA:MEDIA AREA RATIO | PROLIFERATING INTIMAL CELLS (% total) |
|---|---|---|---|
| CONTROL | | | |
| 0 | 17 | 1.07 ± 0.09 | 38.5 ± 4.4 |
| EXPERIMENTAL | | | |
| ~1.0 | 8 | 1.25 ± 0.12 | 48.5 ± 3.7 |
| 7.2 | 7 | 1.43 ± 0.08 | 41.5 ± 1.2 |
| 7.2 | 8 | 1.30 ± 0.14 | 44.5 ± 2.5 |
| therapy initiated 7 days prior to injury | | | |
| average | 23 | 1.40 ± 0.12 | 45.0 ± 2.5 |

Table IV demonstrates that intermittent heparin administration exacerbated intimal hyperplasia and cell proliferation. Beneficial effects of heparin were observed for continuous administration,

EXAMPLE 8

Prolonged continuous release of heparin can be achieved from ethylene-vinyl acetate copolymer (EVAc) matrices, loaded with heparin (Choay heparin 1453, 12,000–18,000 DA U.S.P. 160 units/mg, Paris France) can be prepared as generally described in Edelman et al., *Proc. Nat'l Acad. Sci. USA* (1990) 87:3773–3777. The matrices may be loaded to achieve the desired release rate. For example, 10 mm ×5 mm×1 mm matrices covered by two to six coats EVAc can be used. Release rates can be controlled by the loading. Release rates and duration of release can also be controlled by the size of holes bored into a matrix face. Heparin release can be measured in vitro by incubating the release device with ionically-bound heparin in lactated Ringer's solution at 37° C. for 16 days. Aliquots of solution are sampled at regular intervals and their heparin content assayed using the metachromasia of AzureA (Fisher Scientific Co., Fairlawn, N.J.) at 620 nm. See, Gundry et al. Ann. Surg. (1984) 148:191–194. By increasing the number of copolymer coats and decreasing the size of the holes bored in the coats, more prolonged release is obtained.

Other embodiments are within the following claims.

We claim:

1. A method of regulating repair of a wall of luminal tissue following injury at a location on said wall, said method comprising, administering outside said luminal tissue wall at said location, a biocompatible compound-releasing system, said biocompatible compound-releasing system releasing a smooth muscle cell antiproliferative agent into said wall at said location, said releasing taking place over a period of at least 24 hours and being characterized by a rate and a dosage that is selected to be:

a) high enough to control proliferation of smooth muscle cells in said wall at said location; and b) low enough to substantially avoid systemic levels of said agent that are high enough to control proliferation of smooth muscle cells at a location remote from said location.

2. The method of claim 1 in which the smooth muscle cell antiproliferative agent is heparin and the release rate is low enough to avoid transport of said heparin through said wall to establish a heparin level in the blood system equivalent to an anticoagulant heparin level that would have a discernable effect on clotting function as measured by activated prothrombin time (aPTT).

3. The method of claims 1 or 2 in which the agent is heparin and said heparin is administered at a rate of less than 110 mg/day.

4. The method of claim 3 in which the heparin is administered at a rate less than 20.0 μmg/hr (0.48 mg/day).

5. The method of claim 4 in which the heparin is administered at a rate less than 5.0 μg/hr (0.12 mg/day).

6. The method of claim 5 in which the heparin is administered at a rate less than 0.5 μg/hr (0.012 mg/day).

7. The method of claim 1 in which the agent is delivered locally to a site of vascular injury from the perivascular space at the site of the injury.

8. The method of claim 1 in which the agent is administered substantially continuously over a period of at least 5 days.

9. The method of claim 8 in which the agent is administered substantially continuously over a period of at least 10 days.

10. The method of claim 3 in which the biocompatible compound-releasing system is a polymeric based releasing system.

11. The method of claim 1 in which the biocompatible compound-releasing system is an infusion pump.

12. The method of claim 1 in which the tissue comprises a portion of the vascular system.

13. The method of claim 12 in which the tissue comprises an artery.

14. The method of claim 1 in which the tissue comprises a portion of the reproductive system.

15. The method of claim 14 in which the tissue comprises a fallopian tube.

16. The method of claim 14 in which the tissue comprises the vas deferens.

17. The method of claim 1 in which the tissue comprises a portion of the genitourinary system.

18. The method of claim 17 in which the tissue comprises the ureter or the prostate gland.

19. The method of claim 1 in which the tissue comprises a portion of the gastrointestinal tract.

20. The method of claim 19 in which the tissue comprises the bowel.

21. The method of claim 1 in which the tissue comprises a portion of the pulmonary system.

22. The method of claim 21 in which the tissue comprises the trachea or the bronchial tree.

23. The method of claim 2 the heparin is anticoagulant heparin.

24. The method of claim 2 in which the heparin is non-anticoagulant heparin.

* * * * *